US008597604B2

(12) United States Patent
Ahn

(10) Patent No.: US 8,597,604 B2
(45) Date of Patent: Dec. 3, 2013

(54) TRICALCIUM PHOSPHATES, THEIR COMPOSITES, IMPLANTS INCORPORATING THEM, AND METHODS FOR THEIR PRODUCTION

(75) Inventor: Edward S. Ahn, Dover, MA (US)

(73) Assignee: Pioneer Surgical Technology, Inc., Marquette, MI (US)

( * ) Notice: Subject to any disclaimer, the term of this patent is extended or adjusted under 35 U.S.C. 154(b) by 0 days.

(21) Appl. No.: 13/228,216

(22) Filed: Sep. 8, 2011

(65) Prior Publication Data

US 2011/0318402 A1 Dec. 29, 2011

Related U.S. Application Data

(62) Division of application No. 10/635,402, filed on Aug. 6, 2003, now Pat. No. 8,029,755.

(51) Int. Cl.
*C01B 15/16* (2006.01)
(52) U.S. Cl.
USPC ........... 423/311; 423/305; 423/308; 423/309; 424/423; 623/26
(58) Field of Classification Search
USPC .................. 423/311, 305, 308, 309; 424/423; 623/26
See application file for complete search history.

(56) References Cited

U.S. PATENT DOCUMENTS

| 4,717,556 | A |   | 1/1988 | Kawamura et al. |
|---|---|---|---|---|
| 5,137,534 | A |   | 8/1992 | Sumita |
| 5,185,177 | A |   | 2/1993 | Kijima et al. |
| 5,322,675 | A |   | 6/1994 | Hakamatsuka et al. |
| 5,569,442 | A |   | 10/1996 | Fulmer et al. |
| 5,571,493 | A |   | 11/1996 | Fulmer et al. |
| 5,658,332 | A |   | 8/1997 | Ducheyne et al. |
| 5,676,976 | A |   | 10/1997 | Lee et al. |
| 5,681,872 | A |   | 10/1997 | Erbe |
| 5,683,667 | A |   | 11/1997 | Fulmer et al. |
| 5,782,971 | A |   | 7/1998 | Constanz et al. |
| 5,783,217 | A |   | 7/1998 | Lee et al. |
| 5,820,632 | A |   | 10/1998 | Constanz et al. |
| 5,914,356 | A |   | 6/1999 | Erbe |
| 5,939,039 | A |   | 8/1999 | Sapieszko et al. |
| 6,013,591 | A | * | 1/2000 | Ying et al. ........................ 501/1 |
| 6,027,742 | A |   | 2/2000 | Lee et al. |
| 6,117,456 | A |   | 9/2000 | Lee et al. |
| 6,187,046 | B1 |   | 2/2001 | Yamamoto et al. |
| 6,207,218 | B1 |   | 3/2001 | Layrolle et al. |
| 6,214,368 | B1 |   | 4/2001 | Lee et al. |
| 6,287,341 | B1 |   | 9/2001 | Lee et al. |
| 6,441,073 | B1 |   | 8/2002 | Tanaka et al. |
| 6,458,162 | B1 |   | 10/2002 | Koblish et al. |
| 6,569,396 | B1 |   | 5/2003 | Yanagi et al. |
| 6,840,961 | B2 |   | 1/2005 | Tofighi et al. |
| 6,949,251 | B2 |   | 9/2005 | Dalal et al. |
| 7,318,841 | B2 |   | 1/2008 | Tofighi et al. |
| 2002/0127720 | A1 |   | 9/2002 | Erbe et al. |
| 2002/0165616 | A1 | * | 11/2002 | Heide et al. ................. 623/23.56 |
| 2003/0120351 | A1 |   | 6/2003 | Tofighi et al. |

FOREIGN PATENT DOCUMENTS

| JP | 7-031673 A | 2/1995 |
|---|---|---|
| JP | 2001-054564 A | 2/2001 |
| JP | 2003-180814 A | 7/2003 |
| WO | WO 03/011343 A1 | 2/2003 |
| WO | WO 03/030956 A2 | 4/2003 |

OTHER PUBLICATIONS

Ahn, "Nanostructured Apatites as Orthopedic Biomaterials," (*Ph.D. Dissertation, Massachusetts Institute of Technology*) 1-93 (Jun. 2001).
Akao, M., et al., "Dense Polycrystalline Beta-Tricalcium Phosphate for Prosthetic Applications," *J. Mater. Sci.*, 17: 343-346, (1982).
Cuneyt-Tas, A., et al., "An Investigation of the Chemical Synthesis and High-Temperature Sintering Behavior of Calcium Hydroxyapatite (HA) and Tricalcium Phosphate (TCP) Bioceramics," *J. Mater. Sci. Mater. Med.*, 8: 91-96, (1997).
Deputa, A., et al., "Preparation of Calcium Phosphate Powders by Water Extraction Variant of Sol-Gel process," *CRC Press: Hydroxyapatite and Related Materials*, 263-268 (1994).
Dong, J., et al., "Promotion of Bone Formation Using Highly Pure Porous Beta-TCP Combined With Bone Marrow-Derived Osteoprogenitor Cells," *Biomaterials*, 23: 4493-4502 (2002).
Fini, M., et al., "A Bone Substitute Composed of Polymethylmethacrylate and Alpha-Tricalcium Phosphate: Results in Terms of Osteoblast Function and Bone Tissue Formation," *Biomaterials*, 23: 4523-4531 (2002).
Hirai, T., et al., "The Preparation of Spherical Calcium Phosphate Fine Particles Using an Emulsion Liquid Membrane System," *Langmuir*, 16: 955-960 (2000).
Kawamoto et al., "Coating of β-Tricalcium Phosphate on Yttria-Partially Stabilized Zirconia Using Magnesium Metaphosphate as an Interlayer," *The Ceramic Society of Japan*, 99(1): 19-22 (1991).

(Continued)

*Primary Examiner* — Ali Soroush
(74) *Attorney, Agent, or Firm* — Leydig, Voit & Mayer, Ltd.

(57) ABSTRACT

Methods for the synthesis of tricalcium phosphates are presented, as well as a series of specific reaction parameters that can be adjusted to tailor, in specific ways, properties in the tricalcium phosphate precursor precipitate. Particulate tricalcium phosphate compositions having an average crystal size of about 250 nm or less are provided. Compositions of the invention can be used as prosthetic implants and coatings for prosthetic implants.

25 Claims, No Drawings

(56) References Cited

OTHER PUBLICATIONS

Kivrak, N., et al., "Synthesis of Calcium Hydroxyapatite-Tricalcium Phosphate (HA-TCP) Composite Bioceramic Powders and Their Sintering Behavior," *J. Am. Ceram. Soc.*, 81: 2245-52 (1998).

Kondoh et al., "Sintering of Tricalcium Phosphate by HIP," *Journal of the Ceramic Society of Japan*, 97(9): 965-967 (1989).

Krajewski et al., "Spectrometric Study of the Thermal Evolution of Mechanochemically Prepared Hydroxyapatite-based Powders," *Cryst. Res. Technol.*, 31(5): 637-646 (1996).

Kumar, R., et al., "RF Plasma Processing of Ultra-Fine Hydroxyapatite Powders," *Journal of Materials Processing Technology*, 113: 456-462 (2001).

Kurashina, K., et al., "Ectopic Osteogenesis With Biphasic Ceramics of Hydroxyapatite and Tricalcuim Phosphate in Rabbits," *Biomaterials*, 23: 407-412 (2002).

Kurokawa, "Preparation of Fine Powder of Calcium Phosphate by using Vacuum Freeze-Drying Processing," *The Report of Government Industrial Research Institute*, 34(7): 210-216 (Jul. 1985).

Kwon et al., "Synthesis and dissolution behavior of $\beta$-TCP and HA/$\beta$-TCP composite powders," *Journal of the European Ceramic Society*, 23(7): 1039-1045 (Jun. 1, 2003).

Lange et al., "Effects of attrition milling and post-sintering heat treatment on fabrication, microstructure and properties of transformation toughened $ZrO_2$," *Journal of Materials Science*, 21: 768-774 (1986).

Lin, F., et al., "Preparation of Biphasic Porous Bioceramics by Heating Bovine Cancellous Bone With $Na_2P_2O_7*10H_2O$ Addition," *Biomaterials*, 20: 475-484, (1999).

Liu, D., et al., "Water-Based Sol-Gel Synthesis of Hydroxyapatite: Process Development," *Biomaterials*, 22: 1721-1730 (2001).

Mathew, M., et al., "Structures of Biological Minerals in Dental Research," *J. Re. Natl. Inst. Stand. Technol.*, 106: 1035-1044, (2001).

Prevey, P., "X-Ray Diffraction Characterization of Crystallinity and Phase Composition in Plasma-Sprayed Hydroxylapatite Coatings," *J. Thermal Spray Techn.*, 9: 369-376, (2000).

Raynaud, S., et al., "Calcium Phosphate Apatites With Variable Ca/P Atomic Ratio I: Synthesis, Characterization and Thermal Stability of Powders," *Biomaterials*, 23: 1065-1072 (2002).

Raynaud, S., et al., "Calcium Phosphate Apatites With Variable Ca/P Atomic Ratio III: Mechanical Properties and Degradation in Solution of Hot Pressed Ceramics," *Biomaterials*, 23: 1081-1089 (2002).

Sayer, M., et al., Structure and Composition of Silicon-Stabilized Tricalcium Phosphate, *Biomaterials*, 24: 369-382, (2003).

Serraj, S., et al., "Effect on Composition of Dry Mechanical Grinding of Calcium Phosphate Mixtures," *J. Biomed. Mater. Res.*, 55: 566-575, (2001).

Slosarczyk, A., et al., "Calcium Phosphate Materials Prepared from Precipitates With Various Calcium: Phosphate Molar Ratios," *J. Am. Ceram. Soc.*, 79: 2539-44, (1996).

Takahashi, H., et al., "Synthesis of Stoichiometric Hydroxyapatite by a "Gel" Route From the Aqueous Solution of Citric and Phosphonoacetic Acids," *Eur. J. Solid State Inorg. Chem.*, 32: 829-835 (1995).

Tenhuisen, K., et al., "Phase Evolution During the Formation of Alpha-Tricalcium Phosphate," *J. Am. Ceram. Soc.*, 82: 2813-2818, (1999).

Toriyama et al., "High Strength $\beta$-Tricalcium Phosphate Ceramics I. Mechanochemical Synthesis of $\beta$-Tricalcium Phosphate," *The Report of Government Industrial Research Institute*, 39(5): 217-223 (May 1990)

Toriyama et al., "High Strength $\beta$-Tricalcium Phosphate Ceramics II. Sintering Behavior of $\beta$-Tricalcium Phosphate," *The Report of Government Industrial Research Institute*, 39(5): 224-228 (May 1990).

Toriyama et al., "Synthesis of Hydroxyapatite-Based Powders by Mechano-Chemical Method and their Sintering," *Journal of the European Ceramic Society*, 16: 429-436 (1996).

Toriyama et al., "Effect of Mixed Addition of $Al_2O_3$ and $SiO_2$ on Mechanical Strength of Sintered $\beta$-Tricalcium Phosphate," *The Ceramic Society of Japan*, 96(8): 837-841 (1988).

Toriyama et al., "Thermal Change of Calcium Deficient Apatite Obtained by Mechanochemical Treatment," *The Ceramic Society of Japan*, 97(5): 554-558 (1989).

Toriyama et al., "Synthesis of $\beta$-Tricalcium Phosphate by Use of Wet Milling," *The Ceramic Society of Japan*, 94(9): 78-82 (1986).

Toriyama et al., "Bending Strength of Hydroxyapatite Ceramics Containing $\alpha$-Tricalcium Phosphate," *The Ceramic Society of Japan*, 95(4): 92-94 (1987).

Toriyama et al., "Sinterable Powder of Mechanochemically Synthetic $\beta$-Tricalcium Phosphate," *The Ceramic Society of Japan*, 95(7): 741-745 (1987).

Toriyama et al., "Effect of MgO Addition on Bending Strength of Sintered $\beta$-Tricalcium Phosphate Prepared by Mechanochemical Synthesis," *The Ceramic Society of Japan*, 95(8): 68-70 (1987).

Toriyama et al., "Estimation of Biocompatibility of High Strength $\beta$-Tricalcium Phosphate Ceramics by a Tissue Culture Method," *The Ceramic Society of Japan*, 98(4): 404-407 (1990).

Toriyama et al., "$\beta$-Tricalcium Phosphate Coating on Alumina Ceramic," *The Ceramic Society of Japan*, 98(9): 1054-1057 (1990).

Traplis, C., et al., "Calcium hydroxyapatite Formation by Sol-Gel Route," *Chimica Chronica New Series*, 23: 205-208 (1994).

Victoria, E., et al., "Synthesis and Characterisation of Biphasic Calcium Phosphate," *Tends Biomater. Artif. Organs*, 16: 12-14 (2002).

Yokogawa et al., "Apatite Coating on Yttria Doped Partially Stabilized Zirconia Plate in the Presence of Water Vaper," *The Ceramic Society of Japan*, 100(4): 602-604 (1992).

Yokogawa et al., "Preparation of Trimagnesium Phosphate by Mechanochemical Reaction," *The Ceramic Society of Japan*, 99(2): 150-152 (1991).

Yokogawa et al., "Tricalsium Phosphate Coating on Zirconia by Using Calcium Metaphosphate and Tetracalcium Phosphate," *The Ceramic Society of Japan*, 99(3): 211-214 (1991).

\* cited by examiner

TRICALCIUM PHOSPHATES, THEIR COMPOSITES, IMPLANTS INCORPORATING THEM, AND METHODS FOR THEIR PRODUCTION

CROSS-REFERENCE TO RELATED APPLICATIONS

This patent application is a divisional of copending U.S. patent application Ser. No. 10/635,402 filed on Aug. 6, 2003, the entire disclosure of which is incorporated by reference herein.

FIELD OF THE INVENTION

The present invention generally relates to bioceramics, particularly tricalcium phosphate bioceramics, composites incorporating these materials, and methods for their production.

BACKGROUND OF THE INVENTION

There is a widely recognized need for an implant material that provides excellent structural support for a variety of clinical applications while providing for osteointegration over acceptable periods of time. Conventional metal implants are designed to ensure mechanical stability of the implanted region to meet short-term mechanical goals but raise a number of longer-term clinical concerns including protuberance over the skin, non-uniform healing, bone atrophy, implant migration and loosening, all of which may lead to a second surgery to remove the implant.

The morbidities associated with metallic implants have stimulated interest in polymeric and resorbable implants compromised of polylactic acid, polyglycolic acid, copolymers thereof, polymethylmethacrylate, polypropylenefumarate, collagen, or collagen-glycoaminoglycans. These devices have not been widely accepted due to a number of clinical complications associated with poor mechanical stability, formation of sinus tracts, osteolysis, synovitis, localized inflammation, and hypertrophic fibrous encapsulation. As a result, a clinical demand for stronger, more biocompatible and resorbable orthopedic implants for use in both load-bearing and non load-bearing applications exists. Such an implant will incorporate a biomaterial possessing the following properties: 1) mechanical stability at the injured site for the required duration to allow adequate healing; 2) biocompatibility with the surrounding host tissue; 3) osteointegration with the host bone; and 4) elimination of aseptic inflammation.

Bioceramics have been identified as biomaterial that may potentially possess the desired properties discussed above. They have found widespread use in craniomaxillofacial, dental, and orthopedic applications as well as oral, plastic, and ear, nose, and throat surgery and are categorized according to their in vivo interaction: bioinert, bioactive, and resorbable. Common bioceramics are alumina, zirconia, calcium phosphate-based ceramics, and glass-ceramic composites.

Bioinert bioceramics include alumina and zirconia, and are characterized as such because the body recognizes them as a foreign object and encapsulates them in fibrous tissue. Furthermore, tissue growth associated with this reaction is used to mechanically fix the inert ceramic article within the body by encouraging tissue ingrowth into surface irregularities or intentionally introduce porosity. Although many ceramic compositions have been tested as implants to repair various parts of the body, few have achieved human clinical application. Problems associated with these ceramics typically involve the lack of a stable interface with connective tissue and/or a mismatch in mechanical properties between the implant and the tissue to be replaced (see Hench in "Bioceramics: from Concept to Clinic," *J. Am. Ceram. Soc.,* 1991, 74, 1487-1510). In the case of bioinert bioceramic materials, only a physical interdigitation of weak fibrous tissue onto the implant surface is obtained. If the strength of this fixation between the surrounding tissue and implant is insufficient which is often the case, then loosening of the bioceramic can occur causing necrosis of the surrounding tissue along with implant failure. For example, when alumina or zirconia implants are implanted with a tight mechanical fit within the body and movement does not occur at the interface with tissue, the implants can be clinically successful. However, if movement does occur, the fibrous capsule surrounding the implant can grow to become several hundred microns thick causing the implant to loosen and leading to clinical failure.

Bioactive bioceramics include hydroxyapatite, bioglass, and bioglass-ceramics. A "bioactive" material is one that elicits a specific biological response at its surface, which results in a beneficial biological and chemical reaction with the surrounding tissue. These reactions lead to chemical and biological bonding to the tissue at the interface between tissue and the bioactive implant, rather than mere ingrowth of tissue into pores of the implant, which only provide mechanical fixation. Hydroxyapatite $(Ca_{10}(PO_4)_6(OH)_2$, JC-PDS 9-432) has been of particular interest in orthopedic and dental application because the composition closely resembles native bone mineral and is inherently bioactive and osteoconductive. Though hydroxyapatite has the potential to be a load bearing implant material, applications have been limited to coatings, porous implants and as the bioactive phase in composites because most conventional calcium phosphate processing techniques have been unable to remove the process related defects in load bearing implants that result in poor mechanical properties. The problems associated with processing hydroxyapatite materials have been solved, at least in part, by the method disclosed in U.S. Pat. No. 6,013,591, which describes the synthesis of nanometer-sized hydroxyapatite grains that can be densified to form a hydroxyapatite structure with improved compressive strength, bending strength, and fracture toughness. These results can be attributed to the reduced flaw sizes inherent in nanocrystalline materials.

Resorbable bioceramics include tricalcium phosphate (TCP), calcium sulfate, and other calcium phosphate salt-based bioceramics. They are used to replace damaged tissue and are eventually resorbed such that host tissue replaces the implant. Problems long associated with resorbable bioceramics are the maintenance of strength, stability of the interface, and matching of the resorption rate to the regeneration rate of the host tissue. Furthermore, the constituents of resorbable biomaterials desirably are metabolically acceptable, since large quantities of material must be digested by cells. This imposes a severe limitation on these compositions. Calcium sulfate typically is used as a rapidly degrading bone filler in cases where mechanical strength is not necessary. α-TCP (α-$Ca_3(PO_4)_2$, JC-PDS 9-348) and β-TCP (β-$Ca_3(PO_4)_2$, JC-PDS 9-169) typically are used when a rapidly degrading bone filler having more mechanical strength than calcium sulfate ($CaSO_4$, JC-PDS 6-0046) is needed. Though calcium sulfate and TCP degrade rapidly, they both suffer from poor mechanical properties that have limited their applications to bone fillers.

Because calcium phosphate biomaterials are intrinsically bioactive and resorbable, they can be tailored for mechanical strength, resorption and bonding with the surrounding tissue through nanostructure. While α- and β-TCP are widely used and while a TCP formulation having mechanical and morphological properties advantageous for prostheses would be very useful, attempts to date have failed to produce reliable structural TCP implants. Accordingly, it is an object of the invention to provide techniques for synthesizing α- and β-TCP materials, and composites thereof, having structural and morphological properties useful for structural implants. In particular, it is an object of the invention to provide synthesis and processing techniques that produce a TCP material that can be densified under conditions that allow microstructural control, reduction or elimination of defects, ease of manufacture, and minimization of cost. It is another object of the invention to obtain TCP materials having enhanced mechanical properties, enhanced bioactivity/osteointegration and a controlled resorption profile by controlling the microstructure during sintering through crystal size, morphology and compositional control during synthesis and processing.

BRIEF SUMMARY OF THE INVENTION

The present invention provides compositions and articles comprising tricalcium phosphate (TCP) materials having a particularly small crystal size and/or particle size. The invention further provides a method of consolidating the TCP into a variety of articles that are either fully dense and defect free, or that possess extensive porosity.

TCP (i.e., α- and/or β-TCP) can be formed into high surface area powders, coatings, porous bodies, and dense articles by a wet chemical approach. This wet chemical approach is preferred because it is versatile, simple, and easy to control, in terms of both the preparative reactions and the characteristics of the reaction product, such as morphology, size, and reactivity. Precursor type, precursor concentration, solvent environment, addition rate of precursors, aging time, aging temperature, and pH during precipitation have been identified as the processing parameters controlling the molecular and structural development of TCP precursor materials. Furthermore, by controlling dry particle formation from the precipitate through washing, drying and comminution, an ultrafine particulate TCP precursor powder can be obtained.

This TCP precursor powder is then transformed into TCP, for example by a calcination step. The calcination temperature can be significantly reduced with the appropriate precipitation conditions permitting the formation of an ultrafine particulate TCP that can enhance packing and densification and lower sintering temperatures. The phase (i.e., α or β) of TCP that is obtained is dependent at least in part on the precipitation and processing conditions and calcinations temperature and environment. Alternatively, a method using microwaves, X-rays, lasers, electron beams or neutron beams can be used to transform precursor powder into TCP.

Dense TCP articles can be fabricated by pressureless or pressure-assisted sintering processes using this ultrafine TCP powder. By reducing the crystal size within an article, the smallest possible defect size is reduced thereby increasing the highest possible strength. In addition, ceramics become more ductile at lower temperatures as the volume fraction of grain boundaries increases allowing grain boundary sliding allowing for rapid superplastic net-shape forming. Furthermore, the resorption profile of dense TCP can be controlled by extending the heat treatment during sintering or through post-sinter thermal cycles to alter the microstructure. The subsequent controlled grain growth can then be used to increase or decrease the resorption rate. This TCP precursor powder is then transformed into TCP, for example by a calcination step. The calcination temperature can be significantly reduced with the appropriate precipitation conditions permitting the formation of an ultrafine particulate TCP that can enhance packing and densification and lower sintering temperatures. The phase (i.e., α or β) of TCP that is obtained is dependent at least in part on the precipitation and processing conditions and calcinations temperature and environment. Alternatively, a method using microwaves, X-rays, lasers, electron beams or neutron beams can be used to sinter TCP, with or without pressure, into a dense article.

Thus, TCP of the invention possesses greater reliability and better mechanical properties as compared to conventional TCP having a coarser microstructure. In addition, the TCP of the invention can be structurally reinforced by incorporating a secondary reinforcing species into the TCP precursor material during nanocomposite processing.

In one aspect, the invention provides a composition including particulate TCP having an average TCP crystal size of about 250 nm or less and an average particle size of about 5 μm or less. In another embodiment, the invention provides TCP compositions having a BET surface area of about 20 $m^2/g$ or greater.

In another aspect, the invention provides an article comprising a consolidated TCP structure having an average crystal size of about 80 μm or less and a density of about 90% of the theoretical density. In yet another aspect, the invention provides an article comprising a consolidated TCP structure having an average crystal size of about 1 μm or less and a porosity of about 20% or greater.

The invention also provides a method of calcining a TCP precursor precipitate at a temperature of about 400° C. to about 1400° C. and recovering a nanostructured TCP article having a BET surface area of about 20 $m^2/g$ or greater and a crystal size of about 250 nm or less. The invention also provides a method that involves calcining a TCP precursor material at a temperature of about 400° C. to about 1400° C. and recovering a nanostructured TCP article having a BET surface area of about 20 $m^2/g$ or greater and an average particle size of about 5 micron or less.

In another aspect the invention provides a particulate TCP composition having an average crystal size small enough that the composition can be sintered to a theoretical density of about 90% or greater by pressureless sintering. In another aspect, a method is provided comprising sintering a composition comprising a TCP to a theoretical density of about 90% or greater by pressure-assisted sintering. The invention also includes a method involving sintering TCP in the absence of any sintering additives.

Other advantages, novel features, and objects of the invention will become apparent from the following detailed description of the invention.

DETAILED DESCRIPTION OF THE INVENTION

The present invention provides methods for the synthesis of nanostructured TCP, processing of nanostructured TCP into implantable articles, and steps for carrying out related methods. Desirably, these methods result in one or more improvements related to (a) microstructural control and design on the nanometer scale, (b) phase uniformity and chemical homogeneity on the molecular level, (c) uniformity of chemical and physical properties, (d) machinability of partially consolidated tricalcium phosphates, (e) sintering behavior, (f) mechanical reliability and strength, (g) net shape forming, (h) manufacturing of porous and dense bodies, (i) formation of composite materials, and/or (j) gene, drug and protein delivery devices.

The inventive synthetic methods preferably lead to exceptional microstructural control over the TCP products. Accordingly, the TCP provided in accordance with the invention preferably can be densified with an ultrafine microstructure leading to reduced flaw sizes, greater reliability, better mechanical properties (e.g., strength and fracture toughness), improved ductility, and enhanced bioactivity compared to conventional polycrystalline TCP having a coarser microstructure. Because of the finer microstructure, TCP of the invention can be densified without the need for sintering aids and at substantially lower temperatures. The nanostructured TCP not only provide superior mechanical properties, but also offer the potential for superplastic net-shape forming for inexpensive rapid prototyping.

The present invention further provides a TCP composition comprising deagglomerated nanometer-sized TCP particles. A wet chemical approach is used in the synthesis of preferred compositions leading to the advantages that compositional homogeneity is provided. Furthermore, the method is versatile and easy to control both in terms of the preparative reactions and the character of the reaction product. The processing can be tailored for different applications such as consolidated/densified TCP articles, porous bodies, coatings, cements, and composites by controlling the morphology, size, and reactivity of the precipitated particles. The TCP compositions of the invention preferably comprise TCP powder having a particle size on the order of several microns or less and a narrow log normal particle size distribution.

Crystal size typically governs bulk properties in a consolidated or densified article prepared from the TCP composition. Minimization of TCP crystal size makes consolidation of the crystals, for example during sintering, easier because smaller crystals can re-arrange and pack more readily with respect to each other, and because agglomeration of crystals prior to densification is minimized which enhances densification. Accordingly, preferably the TCP powder of the invention has an average particle size that approaches the average crystal size of the material. In addition, the bioceramic TCP material of the invention having very small crystal sizes is ideal for use in powders or coatings, and for use with bones. The crystal size of healthy bone is approximately 20-30 nm, and bioceramic material having similar crystal size will be more compatible with bone as a result.

Accordingly, the compositions of the invention comprise particulate TCP having an average crystal size of about 250 nm or less (e.g., about 220 nm or less, about 200 nm or less, or about 180 nm or less). Preferably, the crystal size is about 150 nm or less (e.g., about 130 nm or less), more preferably about 100 nm or less (e.g., about 80 nm or less, or about 50 nm or less), and most preferably about 30 nm or less (e.g., about 20 nm or less). In some embodiments, it is desirable that the particulate TCP have an average crystal size of about 500 nm or more (e.g., about 1 micron or more, about 3 micron or more, about 12 micron or more, or even about 60 micron or more) in order to retard the rate of TCP resorption.

In addition, the compositions of the invention comprise particulate TCP having a small average particle size, in particular an average particle size of about 5 μm or less (e.g., about 3 μm or less, about 2 μm or less, or about 1 μm or less), preferably an average particle size of about 800 nm or less (e.g., about 650 nm or less), more preferably an average particle size of about 500 nm or less (e.g., about 400 nm or less). In some embodiments, it is desirable that the particulate TCP have an average particle size of about 100 nm or more (e.g., about 150 nm or more, or about 200 nm or more). Any combination of preferred particle size and preferred crystal size can define a preferable combination of the invention, for example an average crystal size of about 150 nm or less and an average particle size of about 1 μm or less, etc. Preferably, the crystal size is determined by peak broadening analysis of X-ray diffraction peaks or by TEM, and particle size is determined by laser scatter or diffraction, or by electron microcopy (e.g., TEM or SEM).

Typically, the particulate TCP has a narrow log normal particle size distribution. For example, typically about 25% or more (e.g., about 50% or more, about 75% or more) of the TCP particles have a particle size of about 1 micron or less (e.g., about 100 nm to about 800 nm). Furthermore, 90% or more of the TCP particles have a particle size of less than about 10 microns or less (e.g. about 7.5 microns or less, about 5 microns or less). The crystal size and particle size can be determined by any suitable technique, including for example those techniques described above.

The compositions of the invention preferably comprise TCP particles having a high surface area. Typically, the BET surface area is about 20 $m^2/g$ or greater. Preferably, the BET surface area is about 40 $m^2/g$ or greater (e.g., about 60 $m^2/g$ or greater, or about 80 $m^2/g$ or greater), more preferably about 100 $m^2/g$ or greater (e.g., about 120 $m^2/g$ or greater, or about 150 $m^2/g$ or greater).

The TCP particles can have any suitable morphology, for example the particles can have an aspect ratio of about 1:1 to about 50:1. The morphology of the TCP particles will depend on the desired application. When the TCP particles are to be used to form a densified article, preferably the TCP composition comprises TCP particles that are substantially equiaxed (e.g., having an aspect ratio of about 3:1 or less, about 1.5:1 or less, or about 1:1). When the TCP particles are to be used to form a porous consolidated article or as the reinforcing agent a dense composite article, preferably the TCP composition comprises TCP particles that are whisker-like (e.g., having an aspect ratio of about 3:1 or more, 5:1 or more, or even 10:1 or more).

The TCP compositions of the invention desirably are prepared using a wet chemical approach. The wet chemical approach involves (i) precipating a TCP precursor material (e.g., monetite ($CaHPO_4$), brushite ($CaHPO_4 \cdot 2H_2O$), hydroxyapatite, amorphous calcium phosphate, octacalcium phosphate, or combinations thereof), (ii) recovering the TCP precursor material, (iii) milling the TCP precursor material to form a powder in which the TCP precursor crystals are agglomerated to a minimal extent, and (iv) transforming the TCP precursor powder to form TCP. Preferably, the individual nanocrystals of the precipitated TCP precursor material define individual particles. The method optionally further comprises (v) consolidating and densifying the TCP to form a TCP material or article having useful properties. A wet chemical approach is used in the synthesis of preferred compositions leading to the advantages that compositional homogeneity is provided and the method is versatile and easy to control both in terms of the preparative reactions and character of the reaction product.

In order to produce TCP having properties tailored for a particular application, a series of processing parameters are provided in accordance with the invention that affect the molecular and structural development and chemistry of the TCP precursor material, such as aging temperature, aging time, addition rate of reactants (such as addition rate of calcium nitrate solution to basic ammonium hydrogen phosphate solution in TCP production), solution pH during chemical precipitation, precursor concentration and solvent environment. Parameters affecting the agglomeration and densification of ceramic particles such as milling method, calcination temperature/method, and sintering temperature/method also are provided.

As discussed above, the wet chemical approach involves precipitating a TCP precursor material from a solution containing a calcium salt and a phosphate source. The calcium and phosphate sources can be any suitable sources, many of which are commonly known in the art. For example, the calcium source can be selected from the group consisting of calcium nitrate and any hydrate thereof, calcium nitrite, calcium nitride, calcium acetate and any hydrate thereof, calcium hydroxide, calcium alkoxide (e.g., diethoxide, diisopropoxide, and dibutoxide), calcium carbonate, calcium chloride, calcium chlorite, calcium hypochlorite, calcium chlorate, calcium proprionate, calcium perchlorate, and combinations thereof. Preferably, the calcium source is calcium nitrate. The phosphate source can be selected from the group consisting of ammonium hydrogen phosphate, ammonium dihydrogen phosphate, ammonium phosphate, phosphoric acid, phosphorous alkoxides such as trialkylphosphates (e.g., tributylphosphate or triethyl phosphate) or trialkylphosphites (e.g., tributylphosphite or triethyl phosphite), β-glycerophosphate, butyl acid phosphate, phosphonoacetic acid, phosphorous pentoxide and combinations thereof. Preferably, the phosphate source is ammonium phosphate, ammonium hydrogen phosphate, ammonium dihydrogen phosphate, or a combination thereof.

Desirably, the calcium salt and phosphate sources are formed as separate solutions, stable suspensions, or emulsions that are subsequently combined. The solvent can be any suitable solvent. TCP precursors can be precipitated in water, a polar organic solvent (e.g., methanol, ethanol, isopropanol, acetone, or toluene), or a mixture thereof. If water and a polar organic solvent are used as a mixture, the polar organic solvent desirably is miscible with the water. Preferably, the TCP precursor powder is precipitated from a mixture of water, alcohol, oil and surfactant. If water or a water and polar organic solvent mixture is used, water soluble calcium salts such as calcium nitrate and any hydrate thereof, calcium nitride, calcium nitrite, calcium acetate and any hydrate thereof, calcium hydroxide, calcium chloride, calcium chlorite, calcium hypochlorite, calcium chlorate, calcium perchlorate, and combinations thereof and water soluble phosphate salts such as ammonium hydrogen phosphate, ammonium dihydrogen phosphate, ammonium phosphate, phosphoric acid, β-glycerophosphate, butyl acid phosphate, phosphonoacetic acid, and combinations thereof preferably are used.

The calcium source solution and phosphate source solution can have any suitable concentration. Typically, the concentration of the phosphate source solution is about two-thirds the concentration of the calcium source solution. Desirably, the calcium source solution has a concentration of about 2 M or less (e.g., about 1.5 M or less, or about 1 M or less). Optimal physical and chemical properties of the precipitate TCP precursor material are obtained when relatively low source solutions are used, although yields of the TCP precursor precipitate are reduced when using lower concentration solutions. Accordingly, calcium source solution concentrations of about 0.1 M to about 1.5 M (e.g., about 0.12 M to about 1 M, or about 0.15 M to about 0.5 M) are preferred. The phosphate source solution typically has a concentration of about 1.3 M or less (e.g., about 1 M or less, or about 0.6 M or less). Preferably, the phosphate source solution has a concentration of about 0.05 M to about 1 M (e.g., about 0.07 M to about 0.6 M, or about 0.1 M to about 0.3 M).

Preferably, the TCP precursor material is precipitated from calcium source solutions and phosphate source solutions having a molar ratio of calcium to phosphorous of about 1 to about 2 (e.g., about 1.2 to about 1.8). More preferably, the molar ratio of calcium source to phosphorus source is about 1.4 to about 1.6, more preferably about 1.5 (i.e., 3:2). The TCP precursor material can be formed by addition of a calcium source solution to a phosphate solution, by addition of a phosphate source solution to a calcium source solution, or by simultaneous mixing of a calcium salt solution and a phosphate source solution. Preferably, the calcium salt solution is added to the phosphate source solution.

Control of the mixing rates (e.g., addition rates) of the calcium source to the phosphate source (or alternatively the phosphate source to the calcium source) is advantageous for controlling the size of the resulting TCP precursor crystallites. Desirably, the addition rate of the calcium source to the phosphate source (or vice versa) is about 0.1 mmol/min or more (e.g., about 1 mmol/min or more, about 10 mmol/min or more, about 50 mmol/min or more, or even about 100 mmol/min or more). Preferably, the mixing rate is very large (e.g., instantaneous mixing is most preferred); however, the actual mixing rate typically is limited by the mixing/agitation equipment being used and generally is about 1 mol/min or less (e.g., about 0.8 mol/min or less, or about 0.6 mol/min or less). Preferably, the mixing rate (e.g., addition rate) is about 1 mmol/min to about 1000 mmol/min, more preferably about 10 mmol/min to about 500 mmol/min.

The pH of the calcium and phosphate solutions has been found to be an important parameter for controlling the type of TCP precursor material that is formed. Desirably, the TCP precursor material is precipitated from a solution having a pH of from about 5 to about 11, more preferably from about 7 to about 10. When the solution pH is about 5 or 6, the TCP precursor material typically comprises monetite, brushite, or a combination thereof. When the solution pH is 10 or above, the TCP precursor material typically comprises a poorly crystalline apatitic calcium phosphate material. When the solution pH is about 7 to about 10, the TCP precursor material typically comprises predominantly amorphous calcium phosphate, octacalcium phosphate ($Ca_8H_2(PO_4)_6 \cdot 5H_2O$), apatitic TCP, or a combination thereof. The pH of the precursor solutions can be adjusted by addition of one or more common pH adjustors. The pH adjustor can be any suitable pH adjustor, for example nitric acid, acetic acid, ammonium hydroxide, or tetramethylammonium hydroxide (e.g. tetraethylammonium hydroxide or tetrabutylammonium hydroxide). Preferably, the pH adjustor is nitric acid, ammonium hydroxide, or a combination thereof.

The precipitated TCP precursor material is then recovered from the reaction mixture, for example by filtering, filter pressing, centrifugation, or settling and decantation. Preferably, the TCP precursor material is aged prior to recovery. The TCP precursor material can be aged at any suitable temperature and for any suitable amount of time. Typically, the TCP precursor material is aged at a temperature between about 0° C. and about 90° C., preferably between about 5° C. and about 50° C., and more preferably between about 10° C. and about 30° C. (e.g., about 20° C.). Typically, the TCP precursor material is aged for about 1 minute or more (e.g., about 30 minutes or more, or about 60 minutes or more). Preferably, the TCP precursor material is aged for about 2 hours or more (e.g., about 5 hours or more, about 10 hours or more, about 30 hours or more, about 50 hours or more, or even about 100 hours or more). After aging, the TCP precursor material can be collected and then redispersed in a solution having the same solvent and pH as the reaction solution.

The recovered TCP precursor material desirably is dried to form a powder and then is milled. The dry TCP precursor powder can be milled by any suitable method and in the absence or presence of any suitable solvent. Preferably, the dry TCP precursor powder is milled in the presence of anhydrous alcohol, acetone, toluene, or a combination thereof. After milling, the dry TCP precursor powder is dried again.

The dried and milled TCP precursor powder is then transformed into a TCP powder, preferably a nanocrystalline TCP powder. Typically, the TCP precursor powder is calcined under a set of conditions that allow dehydroxylation and production of a robust TCP material having the properties described above. Desirably, calcination of the TCP precursor material produces a pure phase α-TCP or β-TCP, although many other products can be formed. Such other products can include mixed-phase materials, for example hydroxyapatite/α-TCP, hydroxyapatite/β-TCP, α-TCP/β-TCP, and hydroxyapatite/α-TCP/β-TCP. The composition and properties of the TCP material formed by calcination will depend, at least in part, on the calcination conditions, such as the temperature, temperature ramp rate, time, cooling rate, and oven atmosphere. Desirably, the calcination temperature is about 400° C. to about 1400° C. (e.g., about 500° C. to about 1300° C., or about 600° C. to about 1200° C.). Pure phase β-TCP typically is formed by calcining in vacuum at a temperature of about 400° C. to about 900° C. (e.g., about 600° C. to about 800° C.). Pure phase α-TCP typically is formed by calcining at a higher temperature of about 1000° C. to about 1400° C. (e.g., about 1100° C. to about 1250° C.). A mixed α-TCP/β-TCP can be formed by soaking the TCP precursor powder at a first calcination temperature that is greater than 1000° C. (i.e., to allow for full or partial formation of α-TCP) and then soaking the TCP precursor powder at a second temperature that is less than 1000° C. (i.e., to allow for partial formation of β-TCP). Of course, a mixed α-TCP/β-TCP material also can be produced by soaking the TCP precursor powder at a first temperature that is less than 1000° C. (i.e., to allow for full or partial formation of β-TCP) and then soaking the TCP precursor powder at a second temperature that is greater than 1000° C. (i.e., to allow for partial formation of α-TCP).

The ramp rate will depend in part on the type of calcination apparatus that is being used and the type of material being calcined. The ramp rate typically is very rapid and is limited only by the ability of the oven being used to produce a linear well-controlled heating temperature. When the TCP precursor material further comprises an organic material that is to be removed by heating, the ramp rate can be slower to ensure complete removal of that organic material.

The calcination time typically is about 15 min or more (e.g., about 30 min or more, or about 1 hour or more) and about 15 hours or less (e.g., about 12 hours or less, or about 10 hours or less). Preferably, the calcination time is about 1 hour to about 4 hours, more preferably about 1.5 hours to about 2.5 hours (e.g., about 2 hours). Generally, short calcination times (e.g., about 1 hour or less) produce composite TCP materials having smaller crystal sizes, while longer calcination times (e.g., about 4 hours or more) produce pure phase TCP having larger crystal sizes. A calcination time of about 1 hour to about 4 hours typically produces pure phase nanocrystalline TCP powder. The cooling rate (i.e., quenching rate) following calcination will depend on the type of material being produced. For example, when producing α-TCP the cooling rate desirably is rapid to avoid formation of β-TCP. Contrastingly, when producing β-TCP the cooling rate is less important.

The TCP precursor material desirably is calcined in the presence of a reducing atmosphere. The reducing atmosphere can be any suitable reducing atmosphere; for example, the atmosphere can be a vacuum or a gaseous atmosphere comprising nitrogen, argon, helium, hydrogen, and mixtures thereof. Preferably, the reducing atmosphere is a vacuum or a gaseous atmosphere comprising nitrogen.

As an alternative to the thermal treatments (e.g., calcination) typically used to form α- or β-TCP from the TCP precursor material, X-rays, microwaves, electron beam, or other similar radiation can be used to form TCP from the TCP precursor material and still maintain small crystal sizes. By controlling the intensity of the radiation beam and length of exposure, the desired TCP phase can be formed. For example, β-TCP can be transformed into α-TCP having an average crystal size of about 50 nm by exposure to a high intensity and high energy X-ray beam for about 5 minutes.

Using TCP synthesis via the wet chemistry route provided in the invention, a variety of useful applications are realized. First, TCP powders are provided which can be used as bone grafts, bone substitutes, void fillers, pastes, or cements. Second, TCP powders can be used to form TCP coatings including, for example, thermal spray coatings, liquid-based coatings, sputtered coatings, vapor-phase coatings, coatings via wet chemical methods, and the like, many of which are known in the art. Such coatings can benefit from the composition of the invention as the very small particle size results in higher-quality and better-adherent coatings. Porous coatings can be made by admixing an organic species with the bioceramic, forming the coating, and burning out the organic material. Similarly, self-assembled surfactants can be used to form very small pores. For larger pore articles, a polymer can be admixed with the bioceramic crystalline powder and burned out after solidification. Third, the TCP compositions of the invention are easily formable by net shape forming, green machining, or machining after sintering because of their small crystal and particle size.

In one aspect of the invention, the TCP compositions are provided as consolidated particulate TCP, where "consolidated" is meant to define a collection of TCP particles that forms a self-supporting structure. TCP can be consolidated by any suitable technique, for example by providing particulate TCP in a press and compressing the TCP to form an article. The consolidated particulate TCP can be dense or porous. It has generally been relatively straightforward to make porous ceramic articles, but significantly more difficult to make dense ceramic articles. The very small TCP particle size of the invention allows formation of very dense articles. Such dense, strong materials can be used as implants, in particular as load-bearing implants (e.g., dental and orthopedic implants) where strength is required, such as pins, screws, threaded bodies, inter-body spacers, and plates for fracture fixation and fusion, spinal fusion, ball joints for hips, crowns for teeth, etc. The consolidated article also can be formed into the shape of a prosthesis, or can define at least part of a prosthesis such as an exterior coating on a prosthesis. In a particularly preferred embodiment, the consolidated and densified TCP article is used as a spinal implant, an internal or external fixation implant, or an implant for soft tissue attachment, the shapes and dimensions of which are commonly known in the art. Spinal implants can be in the form of a screw and plate, a vertebral body replacement, or an inter-body spacer. In other preferred embodiments, a densified TCP article of the invention can be modified so as to have a bored hole that is filled with a secondary additive such as a polymeric additive (e.g., a polymer sponge, or collagen) which optionally contains one or more biological or pharmaceutical additives as described above.

The consolidated TCP article can have any suitable dimensions. The dimensions will depend on how the consolidated TCP article is being used, for example, the type of implant, prosthesis, or implant/prosthesis coating. The dimensions for such articles are commonly known in the art. Typically, the consolidated TCP article will have a minimum dimension of about 0.5 cm or greater (e.g., 0.8 cm or greater, about 1 cm or greater, or about 2 cm or greater). For example, when used as an exterior coating on a prosthesis, the consolidated TCP article is about 0.5 μm thick or greater (e.g., about 1 μm or greater) in at least one region, and has a lateral dimension of about 0.5 cm or greater (e.g., about 1 cm or greater) relative to the article coated. In some embodiments, the consolidated TCP article has a maximum dimension of about 10 cm or less (e.g., about 7.5 cm or less, or about 5 cm or less).

Typically, the consolidated article has an average crystal size (e.g., grain size) of about 80 μm or less (e.g., about 75 μm or less, about 50 μm or less, or about 25 μm or less). Preferably, the consolidated article has an average crystal size of about 10 μm or less (e.g., about 1 μm or less, about 750 nm or less, about 500 nm or less, or about 300 nm or less). In some embodiments, it is desirable that the consolidated article has an average crystal size of about 100 nm or more (e.g., about 150 nm or more, or about 200 nm or more). The consolidated article preferably has a crystal size distribution of about ±0.75 (e.g., about ±0.5, about ±0.25, or about ±0.1) times the average crystal size.

The theoretical density of consolidated articles of the invention preferably is about 25% or greater, more preferably about 40% or greater, and even more preferably about 55% or greater. In a preferred embodiment, the TCP powder is formed into a densified particulate TCP article where "densified" is defined as having undergone a densification step to create a self-supporting article. Preferably, the TCP powder is densified to a theoretical density of about 60% or greater (e.g., about 70% or greater, or about 80% or greater). More preferably, the article has a density that is about 90% or more (e.g., about 95% or more, or about 98% or more) of the theoretical density.

The densified articles typically have a compressive strength (ASTM C 1424-99) of about 150 MPa or greater (e.g., about 300 MPa or greater), preferably about 500 MPa or greater (e.g., about 600 MPa or greater, or about 700 MPa or greater). The three-point bending strength (ASTM C1161-94) typically is about 100 MPa or greater (e.g., about 200 MPa or greater), preferably about 300 MPa or greater (e.g., about 400 MPa or greater). Generally, the three-point bending strength is about 700 MPa or less (e.g., about 600 MPa or less). The densified articles typically have a fracture toughness (ASTM C 1421-01a) of about 0.5 MPa•m$^{1/2}$ or greater (e.g., about 1 MPa•m$^{1/2}$ or greater, or about 1.5 MPa•m$^{1/2}$ or greater). Generally, the fracture toughness is about 5 MPa•m$^{1/2}$ or less (e.g., about 4 MPa•m$^{1/2}$ or less). Such densified TCP articles can be partially or fully transparent. Preferably, the articles are able to transmit about 50% or more (e.g., about 70% or more, or about 90% or more) light having a wavelength in the range of about 150 nm to about 1,000 nm.

The ability to readily densify the TCP material of the invention indicates that the TCP material also is of a quality that can make it very useful for applications that do not necessarily require density. That is, densification can be used as a screening test for a particularly useful composition, and many compositions of the invention are referred to as densifiable under certain conditions but need not necessarily be densified. As such, the TCP compositions of the invention can also be used to make relatively porous materials/articles for use in applications requiring high-surface-area, flowable, castable materials such as cement for teeth, cement for cranial surgery, and the like. In some cases, porosity can be tailored for a particular purpose such as for bone ingrowth where pores of approximately 200 μm may be desirable.

The porosity of these materials/articles desirably is about 20% or greater. Preferably, the porosity is about 30% or greater (e.g., about 40% or greater, or about 50% or greater). More preferably, the porosity is about 60% or greater (e.g., about 70% or greater). The average pore size typically is about 300 μm or less (e.g., about 200 μm or less, about 150 μm or less, about 100 μm or less). Preferably, the average pore size is about 50 μm or less (e.g., about 20 μm or less, or about 10 μm or less). Typically the average pore size is about 25 nm or more (e.g., about 50 nm or greater, about 100 nm or greater). Preferably, the average pore size is about 200 nm or greater (e.g., about 500 nm or greater, or about 1 μm or greater).

The consolidated porous articles can have a compressive strength (ASTM C1424-99) of about 50 MPa or greater (e.g., about 100 MPa or greater, or about 150 MPa or greater). In addition, the consolidated porous articles can have a three-point bending strength (ASTM C1161-94) of about 20 MPa or greater (e.g., about 40 MPa or greater, or about 60 MPa or greater). Generally, the compressive strength is about 500 MPa or less and the three-point bending strength is about 400 MPa or less. The consolidated porous articles typically have a fracture toughness (ASTM C1421-01a) of about 0.2 MPa•m$^{1/2}$ or greater (e.g., about 0.5 MPa•m$^{1/2}$ or greater). Generally, the fracture toughness is about 1 MPa•m$^{1/2}$ or less.

In other embodiments, the densified article comprising TCP has a void volume of about 75% or less (e.g., about 50% or less, about 25% or less about 10% or less or about 5% or less). Such a densified article need not entirely consist of TCP, rather the article can be a biphasic or composite TCP article. For example, the article can consist of a porous TCP structure, wherein the porosity is filled in by the presence of a secondary additive such as a structural additive (e.g., hydroxyapatite, silver, gold, or magnesium alloy) or an organic additive (e.g., a polymer). Such composite materials will be described in further detail herein.

Typically, the consolidated TCP article described above is prepared from a TCP powder (e.g., a calcined TCP powder) by sintering under mild conditions. The consolidated TCP structures can comprise β-TCP, α-TCP, or a mixture thereof. Typically, the calcined TCP powder is compacted and fired at a sintering temperature of about 400° C. to about 1400° C. (e.g., about 600° C. to about 1300° C.). The sintering time typically is about 30 minutes or more (e.g., about 60 minutes or more) and about 3 hours or less (e.g., about 2 hours or less). To form a sintered β-TCP, compacted β-TCP powders are sintered at a temperature of about 1150° C. or less. To form a sintered α-TCP, compacted α-TCP powders are sintered at a temperature of about 1150° C. or more. To form a α-TCP/β-TCP sintered composite, compacted α-TCP powder can sintered at a temperature of about 1150° C. or less, compacted β-TCP powders can be sintered at a temperature of about 1150° C. or more, or a compacted mixture of α-TCP and β-TCP powders can be sintered at a temperature of about 400° C. to about 1400° C. (e.g., about 600° C. to about 1200° C.).

The calcined compositions of the invention can be sintered to a high theoretical density as discussed above without the need for "sintering aids," many of which are known in the art, including glasses and low melting point glassy oxides that become highly viscous and flow freely during sintering but results in an interfacial glassy phase that weakens an article formed therefrom.

In one preferred embodiment, the TCP compositions of the invention are densified without external pressure (i.e., via pressureless sintering). Pressureless sintering generally is carried out at a low sintering temperature and for relatively short periods of time. For example, the sintering time typically is about 2 hours or less, preferably about 1 hour or less, more preferably about 30 minutes or less. Pressureless sintering can be used because of the unique nature of the TCP material of the invention. In particular, the average particle size and particle size distribution of the TCP powder of the invention desirably is such that the composition can be pressurelessly sintered to a theoretical density of about 90% or more, preferably about 95% or more, and more preferably about 98% or more at a sintering temperature of about 400° C. to about 1400° C. (e.g., about 600° C. to about 1200° C.).

In another preferred embodiment, the consolidated and/or densified TCP articles of the invention can be formed by colloidal pressing (i.e., wet pressing), hot pressing, or hot isotactic pressing. Colloidal pressing is a process by which a stabilized sol of TCP precursor material, optionally containing binders or lubricants, is uniaxially pressed in a die to remove the solvent. A stabilized sol of material is defined as a suspension of particles, which do not undergo sedimentation appreciably over time. Frits within the die allow the solvent to escape as the die is pressurized while trapping the solid particles. Once enough solvent is removed to obtain a solid pellet, the pellet is removed and is carefully dried to prevent drying stresses from cracking the pellet. After fully drying the pellet, the pellet is cold isostatically pressed (CIPed) and then undergoes pressureless sintering as discussed above. Colloidal pressing prevents particle agglomeration that is often associated with working with a dry powder, and benefits from the lubrication effects of the solvent during pressing, which allow the particles in solution to rearrange into the densest packing.

Hot pressing is a form of pressure-assisted sintering whereby a pressure is applied uniaxially to a powder contained within the die during sintering to obtain a fully dense plate. This plate can then be machined into the desired shape. Hot isostatic pressing is a form of pressure-assisted sintering whereby a pressure is applied isostatically to a formed part. The part can be sintered to closed porosity or can be an encapsulated green body that has prepared by well-known net shape forming techniques such as cold isostatic pressing, green machining slip or gel casting, or injection molding. The pressure-assisted sintering allows for more rapid densification and a lower sintering temperature. Typically, a pressure of about 10 MPa or more and about 1 Gpa or less (e.g., about 500 MPa or less, or about 250 MPa or les) and a sintering temperature of about 400 to about 1200° C. is used in pressure-assisted sintering. Generally, the use of higher sintering pressure enables the use of a lower sintering temperature.

In all of the compositions, articles, and methods described above, the preferred compositions, articles, and products of methods comprise TCP either alone or optionally in combination with a secondary additive to define a composite article. The secondary additive can be a structural, organic, polymeric, biological and/or pharmaceutical additive. The secondary additive can be present in any suitable amount and preferably is present in an amount ranging from about 1% to about 50% (e.g., about 5% to about 40%) by volume, preferably from about 15% to about 35% by volume. In a preferred embodiment, the secondary additive and TCP material are each nanocrystalline so as to form a "nano/nano" composite material.

Composites provided in the invention, in particular zirconia-toughened TCP, possess even better mechanical strength than pure TCP and have the potential as material of choice for load-bearing applications. The chemical precipitation process of the invention can also be modified to provide a variety of other novel products such as coatings, cements, pastes and drug/gene delivery.

Composites of TCP with a secondary additive can be formed by any suitable method. For example, the TCP precursor material can be precipitated from a solvent as described above, wherein the solvent contains, in suspension, one or more secondary additives, or the TCP precursor material can be provided in suspension in a solvent from which is precipitated the secondary additive. Preferably, the TCP precursor material and secondary additive(s) are co-precipitated essentially simultaneously. Alternatively, the TCP precursor material can be calcined or sintered in the presence of the secondary additive. In yet another method, the TCP powder can be independently recovered and the secondary additive independently provided (rather than precipitation from a common solvent or suspension), and subsequently admixed and sintered.

Structural additives can be added to the TCP to structurally reinforce the nanocomposite material. The structural additive can be any suitable structural additive. Suitable structural additives include ceramics, metals, alloys, and combinations thereof. Ceramics preferred for use in composites include metal oxides (e.g., alumina, zirconia, and titania), silicon carbides, silicon nitrides, combinations thereof, and other structural ceramics. Metals preferred for use in composites include Mg, Ti, Ta, Nb, Al, Ni, W, Fe, Mo, Co, Zr, Au, Ag, V, alloys thereof, stainless steel, combinations thereof, and other structural metals. Other suitable structural additives include apatite and carbon. The structural additive can have any suitable size or shape. For example, the structural additive can have the shape of particles, rods, whiskers, plates, nanotubes, or fibers. In particular, structural additives having non-spherical aspect ratios are desirable and contribute to great improvements in the fracture toughness and strength. Preferably, the structural additive is selected from the group consisting of nanocrystalline alumina plates, hydroxyapatite whiskers, carbon fibers or nanotubes, silver particles or rods, zirconia particles or rods, and combinations thereof. The structural additive should be selected to strengthen the composite. The secondary, non-TCP structural component can foam a major or minor component, with the overall composite having at least 10% TCP, preferably at least 20% TCP, more preferably at least 50% TCP.

Zirconia and alumina are used advantageously in compositions when toughening of a composition is desired. Compositions can be formulated based on mechanical properties desired. For example, if a secondary phase is "pinned" at grain boundaries (e.g., forms an intergranular phase), ultrafine crystal sizes can be maintained by preventing grain growth of the major phase, which strengthens the material by reducing the defect size. The secondary phases can also deflect or bridge cracks and transformation toughen absorbing crack energy, thereby strengthening the material.

The organic additive can be any suitable organic additive, for example a surfactant (e.g., a cationic surfactant such as cetyl triammonium bromide or dodecyltrimethylammonium chloride; anionic surfactants such as sodium stearate, calcium stearate, zinc stearate, sodium disopropylnaphtalene sulfonate or other alkali or ammonium citrates, acrylates, sulfonates, sulfates, lignosulfonates, carboxylates and phosphates; and nonionic surfactants such as ethoxylated nonylphenol, ethoxylated tridecyl alcohol, acetylenic diol). The polymeric additive can be any suitable polymeric additive, for example a polymer selected from the group consisting of polylactic acid, polyglycolic acid, polylactic/polyglycolic acid copolymers, polypropylenefumarate, polyhydroxybutyric acid, polyhydroxyvaleric acid, polycaprolactone, polyhydroxycarboxylic acids, polybutyrene succinate, polybutylene adipate, collagen, chitosan, alginate, cellulose, starches, sugars, polypeptides, polyethylene glycol, vinyl pyrrolidones, acrylamides and methacrylates or any of their derivates, or a copolymer micelle such as the triblock copolymer PEO-PPO-PEO, PPO-PEO-PPO, polyvinylpyridine-polystyrene-polyvinylpyridine (PVP-PS-PVP), PS-PVP-PS, PS-PEO-PS, PEO-PS-PEO, etc. The biological additive can be any suitable biological additive, for example plasmid DNA or RNA or proteins (e.g., bone morphogenetic proteins 2, 4, 7). The pharmaceutical additive can be any suitable pharmaceutical additive, for example bisphosphonates (e.g., alendronate) and cis-platinum, antibiotics, anti-inflammatories, anti-arthritism, erythropoeitin, etc.

In one preferred embodiment, the TCP porous articles described above are infiltrated with a secondary additive such as hydroxyapatite to form a fully dense article. This composite article will have sufficient strength for load-bearing applications. After implantation, the TCP will be substantially resorbed leaving a porous structure of the secondary composition (e.g., hydroxyapatite) into which bone will ingrow. In another preferred embodiment, a consolidated article (e.g., an implant) comprising a TCP precursor material such as hydroxyapatite is converted to a TCP composite article (e.g., a biphasic hydroxyapatite/TCP composite article). The TCP precursor material can be converted by any suitable means. Preferably, the TCP precursor material is converted through the use of a laser light source (e.g., x-ray, UV, electron, or neutron beam) as described above. For example, the surface of a consolidated or densified hydroxyapatite article can be converted to α-TCP and/or β-TCP. Using a laser beam is particularly advantageous because the laser can convert the TCP precursor material in predictable ways (e.g., in selected areas of an implant). A biphasic hydroxyapatite/TCP article will have the strength and structural stability of hydroxyapatite combined with the resorptive properties of TCP. The amount of TCP formed on the surface of the article will depend on the penetration of the laser into the surface and the length of time for exposure. Typically, the time of exposure is about 1 min to about 20 min (e.g., about 2 min to about 10 min, or about 3 min to about 7 min). Desirably, about 1 μm to about 250 μm (e.g., about 5 μm to about 125 μm) of the hydroxyapatite surface is converted to TCP, which is more readily resorbed than hydroxyapatite.

The articles and compositions of the invention desirably have a resorption time of about 1 month or more (e.g., about 3 months or more, about 6 months or more, or about 1 year or more). The rate of resorption will depend at least in part on the crystal size of the composition or article. Smaller crystal sizes will be resorbed more rapidly than larger crystal sizes. The desired resorption rate will depend on the application and the crystal size can be tailored to match a desired resorption rate. In some applications, it is desired that the resorption time be about 6 months or more (e.g., about 1 year or more, or about 2 years or more).

The function and advantage of these and other embodiments of the present invention will be more fully understood from the examples below. The following examples are intended to illustrate the benefits of the present invention, but do not exemplify the full scope of the invention.

EXAMPLE 1

Optimization of Nanocrystalline TCP Synthesis For Sintering

The sinterability of nanocrystalline TCP powders can be improved by optimizing synthesis parameters such as precursor concentration, addition rate, pH, aging time and aging temperature to produce a nanocrystalline TCP powder that will sinter to high density (e.g. greater than about 95% theoretical density) while a maintaining a nanocrystalline microstructure by pressureless sintering.

Precursor solutions containing either 7.5 liters aqueous $(NH_4)_2HPO_4$ solution (NHP) or 7.5 liters aqueous $Ca(NO_3)_2$ solution (CaN) are prepared at various concentrations. The precursor solutions contain enough NHP and CaN to maintain a calcium to phosphate ratio of about 3:2. The pH of the calcium and phosphate precursor solutions is adjusted from about 5 to about 11 by adding either concentrated nitric acid or an organic acid such as acetic acid to lower the pH or adding either concentrated ammonium hydroxide or an organic base such as tetramethyl ammonium hydroxide. The precursor solutions are mixed at flow rates ranging from about 20 ml/min to about 240 ml/min using a high-speed and high-shear mixer to achieve near-instantaneous high energy mixing. The precursor solutions can be mixed (e.g., combined) in any order. For example, the CaN solution can be added to the NHP solution, or the NHP solution can be added to the CaN solution for a batch or semi-batch process. Alternatively, the CaN solution and the NHP solution can be simultaneously added to the mixer for a semi-batch or continuous process.

Once the addition has been completed, the combined solutions are stirred and aged at temperatures ranging from about 0° C. to about 90° C. for about 0 to about 100 hours. After aging, the precipitate is collected by centrifugation, filtering or settling and the supernatant is decanted. The precipitate is then redispersed in a solution having the same pH as the decanted supernatant. This washing procedure is repeated two more times. Subsequently, the precipitate is redispersed and washed with anhydrous alcohol (i.e., methanol, ethanol, isopropanol, etc.), acetone or toluene three more times to de-water the precipitate. The now gelatinous precipitate is then dried. The dried TCP precursor powder is then milled in anhydrous alcohol, acetone or toluene and then dried again.

The milled powders are then calcined in nitrogen during the ramp and under vacuum at the soak temperature of about 650° C. for about 2 hours to fully transform the TCP precursor powder into β-TCP. After calcination, the β-TCP powders are uniaxially pressed in stainless steel dies to a pressure of about 150 MPa. These compacted pellets are then cold isostatically pressed (CIPed) at a pressure of about 300 MPa for about 3 minutes. After CIPing, the pellets are then sintered in oxygen by pressureless sintering to a soak temperature of about 1100° C. for about 2 hours to evaluate the sinterability of the calcined TCP powders in terms of density and microstructure.

EXAMPLE 2

Determination of Optimal Conditions—Effect of Precursor Concentration

By varying the precursor concentration, the kinetics of TCP precursor synthesis can be affected. By increasing the precursor concentration, the solubility limit at a given pH is more rapidly exceeded, creating a burst of primary nuclei for crystal growth. However, as the reactants are continually added, the primary nuclei continue to grow rapidly. Consequently, high precursor concentrations resulted in larger crystallite and particle sizes.

In this example, TCP precursor powders can be synthesized with CaN and NHP concentrations as high as 1.5 M and 1.0 M, respectively, at an addition rate of about 250 ml/min, at a temperature of 25° C., at an aging time of 100 hours and at a pH of about 8.5. These conditions will result in a TCP with crystallite sizes greater than about 80 nm, particle sizes about 8 μm, and surface areas less than about 50 m$^2$/g. By reducing the precursor concentration, the primary nuclei grow more slowly. For example, when TCP precursor powders are precipitated from solutions having CaN and NHP concentrations as low as 0.15 M and 0.1 M, respectively, at an addition rate of about 250 ml/min, at a temperature of 25° C., at an aging time of 100 hours, and at a pH of about 8.5, crystallite sizes less than about 30 nm, particles sizes less than about 1 μm and surface areas greater than about 125 m$^2$/g will be achieved. Finally, lower precursor concentrations are preferred because these conditions will result in theoretical densities exceeding 95% after pressureless sintering. When TCP precursor powders synthesized at high precursor concentration are pressurelessly sintered, theoretical densities only about 90% will be achieved. However, high precursor concentration are preferred if the TCP materials produced by these reactions are to be used as a coating, porous bodies, cements, pastes, or void fillers.

EXAMPLE 3

Determination of Optimal Conditions—Effect of Addition Rate

By varying the precursor addition rate, nucleation and crystal growth rates can be controlled. Rapid addition of precursors results in localized high concentrations of precursors, exceeding the solubility of TCP in those regions, which favors nucleation and formation of small crystals. At the maximum flow rate of about 250 ml/min at CaN and NHP concentrations of 0.15 M and 0.1 M, respectively, at a temperature of 25° C., at an aging time of 100 hours and at a pH of about 8.5, TCP crystallite sizes of less than 30 nm, an average particle size about 1 μm and surface areas greater than about 125 m$^2$/g after calcination can be prepared. Furthermore, the use of a high-speed, high-shear, high-energy mixer prevents the formation of non-uniform particle morphology and distribution and ensures chemical homogeneity. Slow addition of precursors results in a regime favoring crystal growth and formation of larger particles. At the minimum flow rate of about 20 ml/min at CaN and NHP concentrations of 0.15 M and 0.1 M, respectively, at a temperature of 25° C., at an aging time of 100 hours and at a pH of about 8.5, crystallite sizes greater than about 80 nm, an average particle size of 3 μm and a surface area less than about 100 m$^2$/g after calcination can be prepared. When sintered, the higher addition rates will result in a theoretical density greater than 95% whereas the lower addition rates will result in a theoretical density only greater than about 90%.

EXAMPLE 4

Determination of Optimal Conditions—Effect of pH

Two parameters govern which phase will form for a given calcium phosphate: 1) the initial calcium to phosphate ratio of the reactants and 2) the pH at which the reaction occurs. In this example, all reactions are conducted with a calcium to phosphorus ratio of about 1.5 to favor the synthesis of the TCP precursor phase at CaN and NHP concentrations of 0.15 M and 0.1 M, respectively, at an addition rate of about 250 ml/min, at a temperature of 25° C., and at an aging time of 100 hours. At an initial pH of about 6, the as-precipitated precursor phase is a monetite/brushite phase. At an initial pH of about 7, the as-precipitated precursor phase is also a monetite/brushite phase. At an initial pH of about 10, the as-precipitated precursor phase is a poorly crystalline apatite. When TCP precursor materials precipitated at a pH about 7 or lower are calcined, the monetite and brushite phases persist and β-TCP does not form. When TCP precursor materials precipitated at a pH about 10 or greater are calcined, the apatitic phase persists. However, β-TCP is formed when the calcination temperature is increased above about 800° C. Use of reaction pHs greater than about 10 is undesirable because hydroxyapatite is the thermodynamically favored phase at those pHs, regardless of the initial Ca/P ratio, requiring the use of higher calcination temperatures to form TCP. At pHs about 7 or below, TCP is soluble and acidic calcium phosphates are favored. These experiments indicate that the preferred pH range is above about 7 and below about 10 for obtaining a TCP precursor that can be calcined at 650° C. to form a β-TCP. TCP powders prepared within this pH range will possess a crystal size of about 50 nm or less, a surface area of about 150 m$^2$/g or more and a narrow particle size distribution with an average size of 1 μm. When sintered under pressureless conditions, a theoretical density of greater than 95% can be achieved.

EXAMPLE 5

Determination of Optimal Conditions—Effect of Aging Time

The crystallinity and structural development of TCP is also affected by varying the aging time of the precipitate. By increasing the aging time, the TCP precursor precipitate undergoes recrystallization via Ostwald ripening. As a result, occluded impurities are removed and crystal strain is reduced as free energy of the crystal decreases, while the crystal structure becomes perfected and the exposed area is decreased. Non-uniform morphologies such as needles, rods, or whiskers redissolve and are recrystallized in more orderly morphologies such as spheres (e.g., having an aspect ratio of about 3:1 or less) with the shapes of the primary particles approaching a homogeneous distribution. Furthermore, longer aging times also ensure that the reagents are fully reacted and precipitate out of the solution. In this example, all reactions occur at CaN and NHP concentrations of 0.15 M and 0.1 M, respectively, at an addition rate of about 250 ml/min, at a temperature of 25° C. and at a pH of about 8.5.

For applications requiring sintering, aging times approaching 100 hours are preferred since TCP possessing a theoretical density greater than 95% with a crystal size less than about 250 nm can be obtained. The TCP powders after aging at about 100 hours will possess a crystal size less than about 50 nm, a surface area greater than about 150 m$^2$/g and a narrow particle size distribution with an average particle size of less than about 1 μm. TCP powders aged at shorter aging times, such as 12 hours, 24 hours, or 48 hours, will possess similar crystal sizes, surface areas and particle size distribution. However, these aging times will not achieve theoretical densities greater than about 95% when sintered because of the non-uniform morphologies.

EXAMPLE 6

Determination of Optimal Conditions—Effect of Aging Temperature

By altering the aging temperature, the crystal nucleation and growth can be controlled. By precipitating at low temperatures below about 30° C., crystal growth can be minimized resulting in finer crystals; however, these materials typically possess poor structural development and possess a chemically and thermally unstable structure. When aged at temperatures above about 30° C., the precipitates undergo greater crystal growth and possess better structural development and chemical and thermal stability. In this example, all reactions occur at CaN and NHP concentrations of 0.15 M and 0.1 M, respectively, at an addition rate of about 250 ml/min, at an aging time of 100 hours and at a pH of about 8.5.

Since the as-precipitated phase is a precursor that requires calcination or a related technique to obtain TCP, conditions favoring a thermally unstable precursor that can be easily transformed into TCP are preferred. In particular, aging temperatures below 30° C. are preferred. Furthermore, lower aging temperatures are preferred for sintering since the diffusivities of these materials are higher than for materials that have undergone higher aging temperatures. However, the solubility of calcium phosphate precipitates increase as temperature decreases. Consequently, the calcium to phosphate ratio in the reactant solutions desirably will correspondingly increase to compensate for the increased solubility. For example, when the calcium to phosphate ratio of the reactant solutions are set to about 1.67, a TCP precursor precipitate with a calcium to phosphate ratio of 1.5 will be obtained when aging at 0° C. After calcination, this TCP powder will possess a crystal with a non-uniform morphology and crystal size greater than about 80 nm, a particle size greater than 3 μm and a surface area greater than about 50 $m^2/g$. When this precipitate is calcined and pressurelessly sintered, a TCP possessing a theoretical density greater than 95% will be obtained with a crystal size greater than about 1 μm. As a result, an aging temperature of below 30° C. is preferred when the stoichiometry of the precursor solutions is adjusted to compensate for the higher solubility at lower temperatures.

When the TCP precursor is aged at about 30° C., the powder properties will be more refined. The resulting TCP will possess uniform crystal morphology, a crystal size of less than 50 nm, a narrow particle size distribution, an average particle size of less than about 1 μm, and a surface area of greater than 150 $m^2/g$. These powders also can be pressurelessly sintered to 95% of theoretical density with a crystal size of less than about 250 nm. When the TCP precursor is aged at about 75° C., the TCP crystals will become increasingly anisotropic. This TCP will possess elongated crystal morphology and size greater than 150 nm, an average particle size of greater than 5 μm, and surface area greater less than about 50 $m^2/g$. These powders could not be pressurelessly sintered to 95% of theoretical density.

SUMMARY OF EXAMPLES 1-6

Nanocrystalline TCP can be synthesized by chemical precipitation followed by calcination. The effects of precursor concentration, pH, addition rate, aging time, aging temperature, and calcination temperature on the crystallite size, stoichiometry, particle size and distribution, morphology, crystallinity and structural development can be examined. By identifying the important processing parameters and the method by which they can be controlled, the crystallite size and process-related defect structures can be reduced to enhance the mechanical properties of bulk TCP. Furthermore, using the parameters to reduce agglomeration, to control the particle morphology and size distribution, and to control the chemical reactivity of the particles, full densification can be achieved at lower sintering temperatures. The XRD patterns of the calcined nano-TCP powders are in good agreement with β-TCP file (JC-PDS 9-169); the peaks are substantially broadened due to the nanocrystalline nature of TCP.

Aging temperatures during precipitation affect the crystal growth rate with room temperature and below being favored. Aging time affects the conversion of the chemical homogeneity, crystallite size, and particle morphology and size distribution. pH affects the solubility of the TCP precursor phase. For TCP synthesis, the preferred pH is above about 7 and below about 10. Precursor addition rate affects the nucleation and crystal growth rates and particle morphology. Fast addition rates are preferred at both high and low precursor concentrations. Precursor concentration affects the rate of reaction.

The nano-TCP precursor phase calcined at 600° C. gives an ultrafine crystal size of about 50 nm, surface areas greater than about 150 $m^2/g$ and narrow particle size distributions with an average particle size of 2.5 μm. The nano-TCP compact has superior sinterability when compared to conventional TCP. The highly densified TCP can be obtained by pressureless sintering at 1100° C.

EXAMPLE 7

Effect of Synthesis Conditions on Calcination Temperature

Unlike hydroxyapatite, neither the α- nor β-phase of TCP is formed from the as-precipitated powders synthesized by the procedure and conditions described in Examples 1-6. The purpose of calcination is to first remove any volatile organics (e.g. alcohol, toluene, acetone) or inorganics (e.g. nitrates etc.) that are adsorbed and then to dehydroxylate the TCP precursor phase (e.g. apatite, amorphous calcium phosphate, octacalcium phosphate) and crystallize it into α- and/or β-TCP.

To achieve these objectives, the TCP precursor powders are calcined in oxygen or other oxidizing atmosphere during the ramp to remove any volatile adsorbed species and under vacuum or other reducing atmosphere (e.g. nitrogen, argon or helium) while at the calcination (e.g., soak) temperature for a period of time to promote dehydroxlation and crystallization of the appropriate TCP phase. To investigate the effect of calcination, the TCP precursor powders prepared in Examples 1-6 are calcined at a soak temperature ranging from about 400° C. to 1400° C. for two hours.

At calcination temperatures typically from about 400° C. to 1000° C., β-TCP (JC-PDS 9-169) is obtained. The lowest calcination temperature required to form β-TCP, 400° C., will be achieved with a CaN and NHP concentrations of 0.15 M and 0.1 M, respectively, at an addition rate of about 250 ml/min, at an aging time of about 100 hours, at any aging temperature of about 25° C. and at a pH of about 8.5. At about a 400° C. calcination temperature, the β-TCP powders will possess a crystal size of about 25 nm, a surface area of about 200 $m^2/g$ and a particle size of about 0.8 μm. At a calcination temperature of about 1000° C. or less, the β-TCP powders will possess a crystal size from about 100 nm, a surface area of about 80 $m^2/g$ and a particle size of about 3 μm.

When this precursor powder is calcined above about 1000° C. to 1400° C., a phase pure metastable α-TCP can be obtained if the powders are rapidly quenched to room temperature. At a calcination temperature of about 1100° C. or greater, a mixed α/β-TCP will be obtained of which the α-TCP forms about 50 vol. %. The α-TCP phase will possess a crystal size of about 150 nm whereas the β-TCP will possess a crystal size of about 125 nm. The composite powder will possess a surface area of about 60 $m^2/g$ and a particle size of about 5 µm. By calcination at a temperature of about 1200° C., a pure α-TCP phase can be obtained. The α-TCP phase will possess a crystal size of about 200 nm, a surface area of about 40 m$^2$/g and a particle size of about 7 µm. At a calcination temperature of about 1400° C., a α-TCP powders having a crystal size of about 300 nm, a surface area of about 30 m$^2$/g and a particle size of about 9 µm can be produced. Alternatively, if the powders are slowly quenched or held at lower soak temperatures during cooling, a mixed α/β-phase is formed. The secondary soak temperature and time determine the relative amount of β-TCP formed and physical properties of the composite powder. When holding at a secondary calcination temperature between 600° C. to about 800° C. for a period of 2 hours to about 24 hours, a secondary β-TCP can be introduced to form a composite powder. At lower temperature and shorter times, a lower volume fraction of β-TCP is formed, typically from about 5 to 20 vol. %. At higher temperatures and longer times, a higher volume fraction of β-TCP is formed, typically from about 50 to 75 vol. %.

EXAMPLE 8

Effect of Precursor and Solvent Environment on the Calcination Temperature Required to Form TCP Typically, TCP precursor powders are calcined to dehydroxylate and crystallize the precursor powders into a TCP phase. Consequently, precursor reactants (calcium salt, phosphate salt, and acid or base) and solvents that can reduce hydroxylation and water retention in the precursor lead to lower calcination temperatures and nanocrystalline crystallite sizes (<100 nm).

When precipitating TCP precursors in an aqueous solution, calcium nitrate and ammonium hydrogen phosphate are the preferred calcium and phosphate sources, respectively. The precursor precipitates are aged at 25° C. for 12 hours and are collected, washed, milled, dried and calcined at 600° C. This β-TCP powder will possess a crystal dimension of less than about 50 nm, a surface area in excess of about 150 m$^2$/g, a narrow particle size distribution with an average particle size of about 0.9 micron, and a calcium to phosphate ratio of about 1.5.

When precipitating TCP precursors from a polar organic solvent, calcium alkoxides or calcium acetates are preferred as the calcium source and phosphoric acid or trialkylphosphates (e.g., tributylphosphate or triethyl phosphate) are preferred as the phosphate source. The precursor precipitates are aged at 25° C. for 12 hours and are collected, washed, milled, dried and calcined at 400° C. This β-TCP powder will possess a crystal dimension of less than about 30 nm, a surface area in excess of about 200 m$^2$/g, a narrow particle size distribution with an average particle size of about 0.9 micron, and a calcium to phosphate ratio of about 1.5.

Alternatively, TCP precursors can be precipitated from solution of water and a polar organic solvent. In this case, calcium alkoxides and trialkylphosphates are the preferred calcium and phosphate sources, respectively. The precursor precipitates are aged at 25° C. for 12 hours and are collected, washed, milled, dried and calcined at 400° C. This β-TCP powder will possess a crystal dimension of less than about 30 nm, a surface area in excess of about 200 m$^2$/g, a narrow particle size distribution with an average particle size of about 0.9 micron and a calcium to phosphate ratio of about 1.5.

EXAMPLE 9

Pressureless Sintering of TCP Powders

β-TCP is calcined at a temperature of about 600° C. in an oxygen/vacuum atmosphere, then uniaxially pressed in steel die to a pressure of about 150 MPa, cold isostatically pressed (CIPed) to a pressure of about 300 MPa, and finally pressurelessly sintered at a temperature of about 800° C. to about 1500° C. in an oxygen atmosphere for about 2 hours at a ramp rate of 5° C./min.

Prior to sintering, the β-TCP powders can be uniaxially pressed in a steel die at a pressure ranging from about 50 MPa to about 1 GPa without detrimentally affecting the sintering process. After uniaxially pressing, these compacts can be CIPed at a pressure ranging from about 50 MPa to the maximum allowable pressure for the particular cold isostatic press. Alternatively, the TCP powder can be poured into a rubber mold without uniaxial compaction and then CIPed.

β-TCP is formed at sintering temperatures ranging from about 800° C. to about 1100° C. At sintering temperatures greater than about 1100° C., a mixed α/β-TCP material is formed whereas at sintering temperatures greater than about 1200° C., a pure α-phase is formed. Sintering temperatures ranging from about 900° C. to about 1100° C. result in theoretical densities greater than about 95% while sintering temperatures ranging from about 1000° C. to about 1100° C. result in theoretical densities greater than about 97% and a crystal size of less than about 500 nm. A high-density α-TCP also can be obtained at sintering temperatures greater than about 1200° C. with crystal sizes larger than about 1 µm. Similar to Example 7, a dense α/β-TCP composite material can be obtained by holding α-TCP powder at lower secondary soak temperature to reintroduce the β-TCP phase. The combination of soak temperature and soak time can be used to control the volume fraction and crystal size of β-TCP formed. Higher soak temperatures will result in a larger volume fraction and crystal sizes of β-TCP while lower soak temperatures will results smaller volume fractions and crystal sizes.

The fracture toughness of the articles sintered by pressureless sintering is measured by an indentation technique. The fracture toughness is less than about 1 to 2 MPa•m$^{1/2}$. Furthermore, bending strengths and equibiaxial flexure strengths are from about 100 MPa to about 250 MPa. The compressive strength is about 500 MPa or greater.

EXAMPLE 10

Hot Pressing of TCP Powders

TCP powders are hot pressed at a pressure of about 50 MPa or higher, at a ramp rate of about 5° C./min, and with a dwell time of about 30 minutes at sintering temperature between about 700° C. and about 1300° C. in an oxygen, hydrogen nitrogen, argon, helium or vacuum atmosphere. Compared to the pressureless sintering process described in Example 9, the addition of a uniaxial pressure during sintering enhances the sintering process by reducing the sintering temperature at which fully densified articles are achieved by several hundred degrees. Furthermore, the reduction of the sintering temperature results in minimized grain growth as well.

Fully densified articles of β-TCP with a crystal size of less than about 500 nm will be obtained by hot pressing at sintering temperatures less than about 1000° C. Similar to Example 9, higher sintering temperatures will result in a fully dense α-TCP while lower secondary soak temperatures after sintering can reintroduce the β-TCP. Furthermore, these densified articles are optically transparent. The application of the uniaxial pressure removes many pores, which are not removed by pressureless sintering. Fracture toughness measurements via indentation show that fracture toughness is increased to between about 1.5 MPa•m$^{1/2}$ and about 3.0 MPa•m$^{1/2}$. Furthermore, bending strengths and equibiaxial flexure strengths are from about 150 MPa to about 400 MPa. The compressive strength is about 700 MPa or greater. Finally, densified articles prepared by hot pressing possess better reliability than articles prepared by pressureless sintering.

EXAMPLE 11

Net Shape Forming and Hot Isostatic Pressing of TCP Powders

Geometrically complex monoliths comprised of TCP are processed in two steps. First, the TCP powder is net shape formed into a green body and secondly, the green body is densified by hot isostatic sintering. Microstructural and mechanical properties analysis can be used to evaluate the process for the net shape forming of geometrically complex TCP monoliths.

Complex shapes are formed by one of four processes. These processes include dry powder compaction, plastic flow, fluid removal, and gelation. Dry powder compaction can be carried out by cold isostatic pressing in a mold to net shape or green machining of the cold isostatically pressed green body. Examples of plastic flow processes include injection molding and extrusion/green machining. Examples of fluid removal processes include slip casting and pressure casting/green machining. Gelation can be carried out by in situ polymerization and gelation using any combination of the following monomer/polymer systems: acrylamides, methacrylates, starches, sugars, alginates, chitosans, or celluloses. Depending on the mold design, the green bodies can be cylinders, tapered pins, blocks, or plates. In addition, the mold design can introduce threading and cannulation. Nanoporosity (~100 nm) can be introduced by changing the morphology of the nanocrystals whereas macroporosity (~150 μm) can be introduced using a polymer spheres that can be removed prior to hot isostatic pressing. To obtain a green part that can be fully densified and possess strength sufficient for a structural application, the green body should possess the following properties: (1) absence of inclusions or impurities, (2) absence of regions of high or low density, and (3) small pore sizes and narrow pore size distribution.

Hot isostatic pressing (HIP) is dependent on the simultaneous application of high temperature and high pressure to densify the part. The advantage of this process is that it can sinter complex shapes and reduce sintering temperatures while decreasing the size of processing related bulk defects. After net shape forming, the green body is either sintered to closed porosity (greater than 95% theoretical density) or encapsulated/vacuum sealed in glass or a metal and then hot isostatic pressed. Typically pressures during HIP of TCP are between about 50 MPa and the greatest operating pressure of the HIP system. Sintering temperatures occur between about 600° C. and about 1500° C. Soak times range from about 10 minutes to about 2 hours. Phase behavior of TCP is similar to those observed in Examples 9 and 10.

TCP articles densified by HIP are typically fully dense (greater than 97% theoretical dense), nanocrystalline (crystal sizes less than 250 nm), and optically transparent. Because critical defect sizes are reduced by preserving nanocrystallinity, and process-related defects have largely been removed through HIP, the fracture toughness and strength of TCP articles is enhanced. For example, fracture toughnesses via indentation testing between about 1.5 MPa•m$^{1/2}$ and about 3.0 MPa•m$^{1/2}$ can be obtained. Furthermore, bending and equibiaxial flexure strength from about 150 MPa to about 400 MPa can be obtained. Compressive strengths greater than about 750 MPa have also can be obtained. Finally, articles produced by HIP possess better reliability than articles prepared by hot pressing.

EXAMPLE 12

Resorption and Bioactivity of TCP

When comparing like powders, coating, porous bodies or dense articles of TCP, the degree of protein adsorption, cell attachment, adhesion, proliferation, and matrix synthesis is a function of the crystal size. For example, protein adsorption, cell attachment, adhesion, proliferation, and matrix synthesis are enhanced for TCP materials having smaller crystal size compared to those with larger crystal size. Accordingly, nanocrystalline TCP having a crystal size or crystal size ranging from about 20 to about 200 nm are preferred for applications requiring high bioactivity. Resorption of TCP into the body also is found to be a function of crystal size when all other properties for powders, cement, pastes, void fillers, coatings, porous bodies and dense articles are similar. Typically, small grain materials resorb more rapidly than coarse grain materials. Using the method of the invention, the TCP crystal and grain sizes can be varied to control the resorption time of these materials when used as a powders, cement, pastes, void fillers, coatings, porous bodies and dense articles.

EXAMPLE 13

TCP Nanocomposites

To further increase the fracture toughness of TCP materials, a porous or dense TCP composite can be formed. In one method, a secondary additive possessing material properties different than those of TCP can be incorporated into the microstructure. Desirably, the secondary additive is stronger than the TCP material, for example, the secondary additive typically possesses a higher fracture toughness, hardness, ductility, and/or strength than the TCP material. The secondary additive can be selected from the group consisting of alumina, titania, zirconia, gold, silver, titanium, nitinol, and combinations thereof. The fracture toughness of the TCP material also can be increased by introducing a secondary additive possessing a non-spherical aspect ratio (e.g., an aspect ratio greater than about 1.5, or about 2). Such secondary additives having non-spherical aspect ratios include, for example, alumina, hydroxyapatite, titania, zirconia, or metallic needles, rods or whiskers or carbon nanotubes, plates, and the like. The secondary additive can have a length on the order of a nanometer to several microns, but should be small enough so as to be easily dispersed during synthesis or as to create processing defects that cannot be removed through pressure-assisted densification.

To synthesize such a composite material, the secondary additive can be highly dispersed in either the calcium salt or ammonium salt solution, and should be present in the volume fraction that is desired in the final composite article. The TCP is then precipitated in the presence of the secondary additive so as to achieve a high dispersion of the secondary additive in the TCP. It is preferred that the secondary additive be fully reacted and crystalline in order to minimize reactions due to pH or the presence of calcium or phosphate ions. The composite precipitate is recovered and processed as previous described. When sintered to full density by methods described in Examples 9-11, the microstructure of the composite material is such that the TCP phase is still nanocrystalline whereas the secondary phase is highly dispersed.

Because the secondary phase is highly dispersed, fracture toughness and strengths enhancements are achieved with smaller volume fractions of the secondary additive. The secondary phases preferably exist in domains of about 1 micron or less in the TCP matrix with the preferred secondary phase dispersed as the finest individual elements in the matrix. Fracture toughness of greater than about 2 MPa•m$^{1/2}$ and bending and equibiaxial flexure strengths of about 200 MPa or greater are easily achieved.

EXAMPLE 14

Calcium Phosphate-Polymer Nanocomposites

Unlike Example 13 where the objective was to improve the mechanical properties of TCP, the presence of calcium phosphates, such as apatites or TCP, in polymer nanocomposites is used to both mechanically reinforce the polymer by increasing stiffness and strength and to increase the bioactivity of the composite article. To achieve these requirements, the calcium phosphate biomaterials desirably are highly dispersed in the polymer phase. Preferably, the calcium phosphate exists in domains of about 1 micron or smaller. More preferably, the calcium phosphate exists in domains on nanometer scale (e.g., about 20 to about 500 nm). To synthesize such polymer nanocomposites, the calcium phosphate nanocrystals should be dispersed in the reaction medium containing the monomer prior to the synthesis of the polymer. Preferred polymers include polylactic acid, polyglycolic acid, polylactic acid/polyglycolic acid copolymers, polypropylenefumarate, polyhydroxybutyric acid, polyhydroxyvaleric acid, polycaprolactone, polyhydroxycarboxylic acids, polybutyrene succinate, polybutylene adipate, and collagen.

EXAMPLE 15

Processing of Porous TCP

As previously discussed in Example 10, a porous TCP can be made by molding TCP with polymer spheres having diameters ranging from about 25 nm to about 300 microns. Once compacted, the polymer spheres are burned out during a high temperature treatment (e.g., calcination or sintering) leaving extensive and interconnected porosity while the pore walls are comprised of nanocrystalline TCP. By controlling the particle size distribution of polymer spheres, the pore size of the TCP across several orders of magnitude can be introduced. The volume fraction is then selected to achieve a particular strength. At high polymer sphere volume fractions, the compressive strength of the material is low. However, there is a critical volume fraction where these is an insufficient volume fraction to form interconnected porous. As an alternative method to forming porous bodies with nanocrystalline walls, a foaming agent may be added to a highly loaded slurry of TCP to create pores. The pores are preserved by the addition of a curing agent such as a polymer or monomer. The slurry is then dried and fired to remove any organic. This method also allows the ability of to form pores with a wide pore size distribution. Another method is to cast a highly loaded slurry with the curing agent into a porous polymer foam. Once dried, the material is fired to remove the organics and polymer foam leaving a porous TCP. Pores smaller than 100 nm can be formed by introducing a surfactant (i.e. cetyl triammonium bromide) or triblock copolymer (i.e. PEO-PPO-PEO) micelles during the precipitation of the TCP precursor or into the slurry. The micelle TCP solution is then processed with polymer spheres, foaming agents or polymer foams to create a porous body with pores ranging from 25 nm to 300 microns in size.

EXAMPLE 16

Bicontinuous Biphasic Calcium Phosphate Composite

In this example, a dense article comprising of two bicontinuous phases of nanocrystalline hydroxyapatite and TCP is proposed. The article would be highly dense (greater than 95% of theoretical density of the composite) and possess a high bending strength. The bicontinuous phases exist in channels with diameters ranging from 1 micron to 300 microns. Furthermore, the crystal sizes of each bicontinuous phase can be separately changed from about 50 nm to about 5 microns.

Once implanted, the TCP phase will resorb at a rate determined by its density, crystal size and channel diameter. As the TCP resorbs, a porous hydroxyapatite emerges from the dense bicontinuous biphasic calcium phosphate composite, and the host tissue begins to infiltrate the porous hydroxyapatite. The resorption rate of the hydroxyapatite is determined by its density, crystal size and channel diameter.

To produce such an article, a porous TCP can be formed according to the method of Example 15. After drying, a highly loaded slurry of hydroxyapatite is poured into the porous TCP. Alternatively, a porous hydroxyapatite body can be formed according to Example 15 and then infiltrated with a TCP slurry. This now bicontinuous biphasic calcium phosphate composite is then sintered according to methods described in Examples 8-10.

EXAMPLE 17

Calcium Phosphate Structures as a Delivery Vehicle for Plasmid DNA, RNA, Proteins, and Drugs The surfaces of a calcium phosphate powder such as TCP or hydroxyapatite are saturated with plasmid DNA or RNA for gene delivery, proteins such as bone morphogenetic proteins (BMPs), or drugs such as bisphosphonates and antibiotics for drug delivery. Once the organic materials have been fully adsorbed to the surface, the powders are recovered and dried. These powders can be used in pastes, cements, coatings, void fillers or implants desiring gene or drug delivery. To form an implant structure, the powders can be CIPed at pressures of about 100 MPa or greater, at temperatures of about 25° C. or higher, and at times of about 5 minutes or greater. By CIPing, the density is increased thereby ensuring sustained delivery of the active agent. Furthermore, the high density of the article allows it to be used as a load-bearing implant.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An article comprising a porous consolidated TCP structure,
   wherein the TCP structure comprises TCP crystals having an average crystal size of about 1 µm or less and an aspect ratio of about 3:1 or more,
   wherein the TCP structure has a porosity of about 20% or greater, and
   wherein the article has a dimension of about 0.5 cm or greater, a compressive strength of about 50 MPa or greater, and a three point bending strength of about 20 MPa or greater.

2. The article of claim 1, wherein the TCP structure has a porosity of about 40% or greater.

3. The article of claim 1, wherein the TCP structure has an average pore size of about 300 µm or less.

4. The article of claim 1, wherein the TCP structure has a compressive strength of about 100 MPa or greater.

5. The article of claim 1, wherein the TCP structure has an average crystal size of about 500 nm or less.

6. The article of claim 1, wherein the TCP structure comprises α-TCP, β-TCP, or a combination thereof.

7. The article of claim 1, wherein the article has a dimension of about 1 cm or greater.

8. The article of claim 1, wherein the article is a prosthesis.

9. The article of claim 1, wherein the article is at least part of a prosthesis.

10. The article of claim 1, wherein the article comprises an exterior coating on a prosthesis.

11. The article of claim 1, wherein the article is a bioactive implant.

12. The article of claim 11, wherein the bioactive implant is an orthopedic or dental implant.

13. The article of claim 1, wherein the TCP structure comprises a secondary additive.

14. The article of claim 13, wherein the secondary additive is an organic additive.

15. The article of claim 13, wherein the secondary additive is a polymeric additive.

16. The article of claim 15, wherein the polymeric additive is selected from the group consisting of polylactic acid, polyglycolic acid, polylactic/polyglycolic acid copolymers, polypropylenefumarate, polyhydroxybutyric acid, polyhydroxyvalerie acid, polycaprolactone, polyhydroxycarboxylic acids, polybutyrene succinate, polybutylene adipate, collagen, chitosan, alginate, celluloses, starches, sugars, polypeptides, polyethylene glycols, vinyl pyrrolidones, acrylamides, methaerylates, copolymer micelles, and combinations thereof.

17. The article of claim 13, wherein the secondary additive is a biological additive.

18. The article of claim 17, wherein the biological additive is selected from the group consisting of plasmid DNA, RNA, proteins, bone morphogenetic proteins, and combinations thereof.

19. The article of claim 13, wherein the secondary additive is a pharmaceutical additive.

20. The article of claim 19, wherein the pharmaceutical additive is selected from the group consisting of bisphosphonates, cis-platinum compounds, antibiotics, anti-inflammatory agents, anti-arthritism agents, erythropoeitin, and combinations thereof.

21. The article of claim 13, wherein the secondary additive is hydroxyapatite.

22. The article of claim 13, wherein the secondary additive is added in an amount of between about 1% and about 50% by volume.

23. The article of claim 1, wherein the TCP structure has a macroporosity and a nanoporosity.

24. The article of claim 1, wherein the TCP structure has an interconnected porosity.

25. The article of claim 1, wherein the article has a resorption time of about 1 month or more.

* * * * *